US00PP08880P

United States Patent [19]

Danziger

[11] Patent Number: Plant 8,880

[45] Date of Patent: Sep. 6, 1994

[54] PETUNIA PLANT NAMED CAS 3

[75] Inventor: Garbriel Danziger, Post Beit Dagan, Israel

[73] Assignee: Florfis AG, Binningen, Switzerland

[21] Appl. No.: 162,352

[22] Filed: Dec. 7, 1993

[51] Int. Cl.[5] ..... A01H 5/00

[52] U.S. Cl. ..... Plt./68.1

[58] Field of Search ..... Plt. 68.1

[56] References Cited

U.S. PATENT DOCUMENTS

P.P.6914 7/1989 Tsuda et al ..... PLT/68.1

*Primary Examiner*—James R. Feyrer

*Attorney, Agent, or Firm*—Foley & Lardner

[57] ABSTRACT

A new and distinct cultivar of Petunia plant named Cas 3, characterized by the combined features of intense red-violet flowers, profuse flowering with comparatively small flowers, vigorous growth habit, long, overhanging plant habit and dark green foliage.

2 Drawing Sheets

The present invention comprises a new and distinct cultivar of Petunia, hereinafter referred to by the cultivar name Cas 3.

Cas 3 was originated from a hybridization made by the inventor Gabriel Danziger in a controlled breeding program in Moshav Mishmar Hashiva, Israel in 1992. The female parent was a seedling designated X 19. The male parent of Cas 3 was a seedling designated Y 59. Both parents are proprietary cultivars used in the breeding program.

Cas 3 was discovered and selected as one flowering plant within the progeny of the stated cross by Gabriel Danziger in 1992 in a controlled environment in Moshav Mishmar Hashiva, Israel.

The first act of asexual reproduction of Cas 3 was accomplished when vegetative cuttings were taken from the initial selection in Dec. 1992 in a controlled environment in Moshav Mishmar Hashiva, Israel, by, or under the supervision of, Gabriel Danziger.

Horticultural examination of selected units initiated in Dec. 1992 and continuing thereafter has demonstrated that the combination of characteristics are herein disclosed for Cas 3 are firmly fixed and are retained through successive generations of asexual reproduction.

Cas 3 has not been observed under all possible environmental conditions. The phenotype may vary significantly with variations in environment such as temperature, light intensity and day length without, however, any variations in genotype.

The following observations, measurements, and comparisons describe plants grown in Hillscheid, Germany, under greenhouse conditions which approximate those generally used in commercial practice.

The following traits have been repeatedly observed and are determined to be basic characteristics of Cas 3, which in combination distinguish this Petunia as a new and distinct cultivar:

1. Intense red-violet flower color.
2. Profuse flowering with comparatively small flowers.
3. Vigorous growth habit, with branches fully extending in all directions from center of plant.
4. Long, overhanging plant habit.
5. Dark green foliage.

Of the commercial cultivars known to the present inventor, the most similar in comparison to Cas 3 is Revolution. Reference is made to attached Chart A which compares certain characteristics of Cas 3 to those same characteristics of Revolution. In general comparison to Revolution, Cas 3 has a more bluish tint of flower color and a somewhat shorter plant habit.

The accompanying photographic drawings show typical flower and foliage characteristics of Cas 3, with colors being as true as possible with illustrations of this type.

The photograph on Sheet 1 illustrates Cas 3 cultivated in a hanging basket.

The photo on Sheet 2 comprises an enlarged showing of single flowers of the new cultivar.

In the following description, color reference ar made to The Royal Horticultural Society Colour Chart. The color values were determined indoors in August. Flowers were taken from plants cultivated in hanging baskets in an open greenhouse in Hillscheid, Germany. For the description, the upper parts of the plants were observed or measured.

Classification:

*Botanical.*—A hybrid of the genus Petunia.

*Commerical.*—Petunia cv Cas 3.

INFLORESCENCE

Plant:

*Growth habit.*—Vigorous, long drooping.

*Plant length.*—110 cm, measured from the base of the stems in the middle of the hanging basket to the tips of the hanging branches (28 week old plants).

*Blooming period.*—Early; begins 9 weeks after propagation of unrooted cuttings, continually flowering thereafter.

Stem:

*Thickness.*—Young branches, 2–2.5 mm; older branches 4 mm.

*Color.*—Medium green, 137 C.

*Pubescence.*—Present.

*Branches.*—10–12 branches per week.

*Length of internode.*—35–40 mm.

Leaf:

*Arrangement on stem.*—Opposite, arranged decussately on stem.

*Shape.*—Ovate or narrow/ovate.

*Size (average).*—Comparatively small; 45 mm long, 26 mm broad, based on largest leaves from a young stem of plant in flower.

*Thickness.*—Medium.

*Color.*—Dark green, 137A.

*Pubescence.*—Present, weak.

Flower:

*Orientation at opening.*—The bud and peduncle form an acute angle with the stem; the open flower and peduncle are oriented approximately at right angles to the stem.

*Type.*—Single.

*Shape.*—Nearly round, comparatively small.

*Diameter.*—54–58 mm.

*Color.*—Upper (inner) surface at opening: 83 B. Under (outer) surface at opening: Somewhat lighter than 83 C. Upper (inner) surface at pollen maturity: Between 74 A and slightly more intense than 78 A. Under (outer) surface at pollen maturity: 80 B near margin. Throat (inner surface): White or light violet. Markings: Black net-shaped veining in the throat, no markings on the corolla.

*Peduncle length.*—25–35 mm.

*Penducle color.*—Green, some anthocyanin near base of flower.

*Reproduction organs.*—Pistil: 1, green. Stamens: 5, fertile. Anther: White, with bluish white pollen. Filament: White.

Resistance: Very good resistance to rain and good heat tolerance.

CHART A

| | Cas 3 | Revolution |
|---|---|---|
| Flower color | Between 74 A and 78 A | 74 A |
| Flower throat | White or light violet with black veining | Looks dark due to very dense net-shaped veining |
| Plant habit (length) | 110 cm | 130 cm |

It is claimed:

1. A new and distinct cultivar of Petunia plant named Cas 3, as illustrated and described.

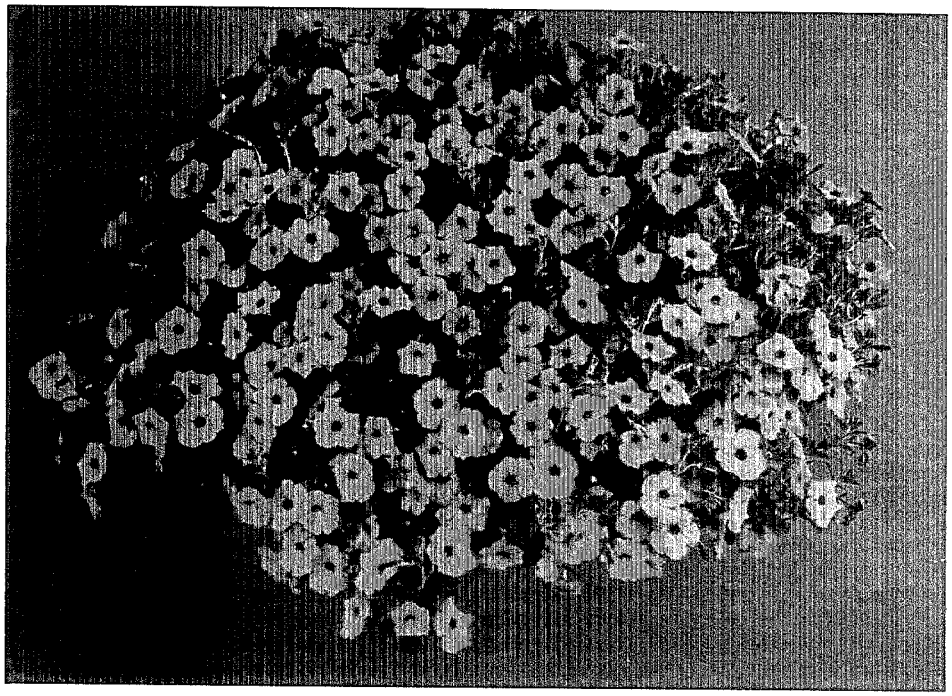

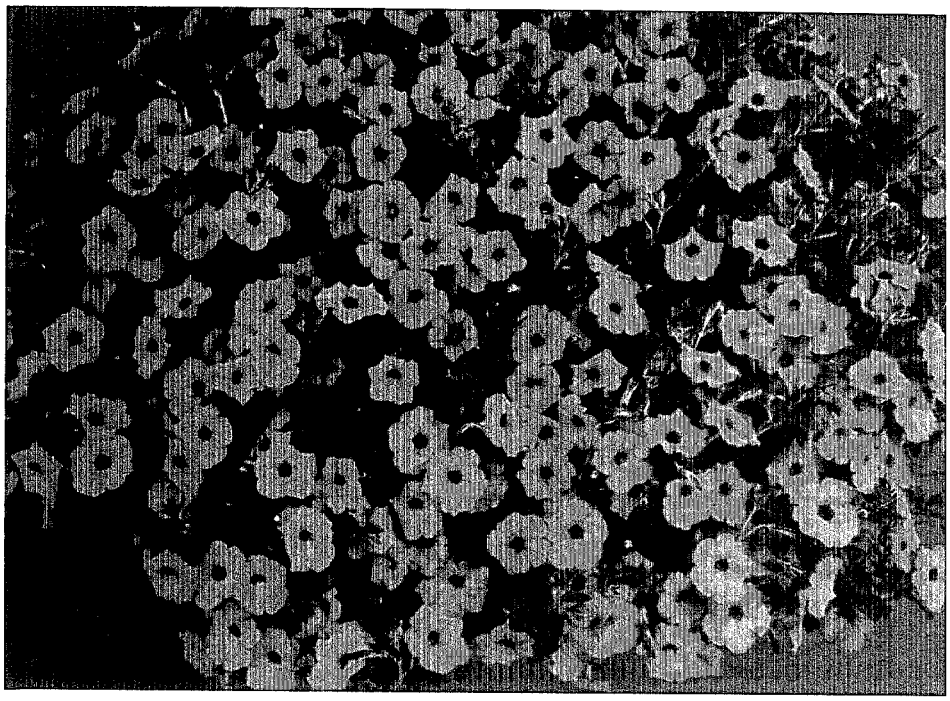

* * * * *